(12) United States Patent
Rigoni (10) Patent No.: US 12,324,932 B2
(45) Date of Patent: Jun. 10, 2025

(54) METHOD AND PLANNING DEVICE FOR PLANNING A LOCALLY SELECTIVE IRRADIATION OF A WORKING AREA, COMPUTER PROGRAM, METHOD AND MANUFACTURING DEVICE FOR ADDITIVELY MANUFACTURING AN OBJECT FROM A POWDER MATERIAL

(71) Applicant: TRUMPF Additive Manufacturing Italia s.r.l., Schio VI (IT)

(72) Inventor: Massimo Rigoni, Asiago (IT)

(73) Assignee: TRUMPF ADDITIVE MANUFACTURING ITALIA S.R.L., Schio Vi (IT)

( * ) Notice: Subject to any disclaimer, the term of this patent is extended or adjusted under 35 U.S.C. 154(b) by 109 days.

(21) Appl. No.: 18/177,139

(22) Filed: Mar. 2, 2023

(65) Prior Publication Data

US 2023/0277871 A1 Sep. 7, 2023

(30) Foreign Application Priority Data

Mar. 3, 2022 (EP) .................................... 22160041

(51) Int. Cl.
*A61N 5/10* (2006.01)
*A61N 5/06* (2006.01)

(52) U.S. Cl.
CPC ............. *A61N 5/1045* (2013.01); *A61N 5/06* (2013.01)

(58) Field of Classification Search
CPC .............................. B22F 10/85; B29C 64/153
See application file for complete search history.

(56) References Cited

U.S. PATENT DOCUMENTS

| | | | |
|---|---|---|---|
| 5,536,467 | A | 7/1996 | Reichle et al. |
| 9,358,729 | B2 | 6/2016 | Hofacker et al. |
| 9,468,973 | B2 | 10/2016 | Ljungblad |
| 9,844,913 | B2 | 12/2017 | Bessac et al. |
| 10,201,962 | B2 | 2/2019 | Teulet |
| 10,315,252 | B2 | 6/2019 | Symeonidis et al. |
| 10,335,901 | B2 | 7/2019 | Ferrar et al. |
| 10,338,569 | B2 | 7/2019 | Crear et al. |
| 10,406,633 | B2 | 9/2019 | Crear et al. |
| 10,471,510 | B2 | 11/2019 | Crear et al. |
| 10,583,529 | B2 | 3/2020 | Gray |

(Continued)

FOREIGN PATENT DOCUMENTS

| | | |
|---|---|---|
| CA | 2869168 C | 12/2020 |
| CN | 105665701 A | 6/2016 |

(Continued)

*Primary Examiner* — Virak Nguon
(74) *Attorney, Agent, or Firm* — LEYDIG, VOIT & MAYER, LTD.

(57) ABSTRACT

A method for planning a locally selective irradiation of a working area with a plurality of energy beams by displacing the plurality of energy beams along a plurality of irradiation vectors over a powder material layer of a powder material arranged in the working area is provided. The method includes assigning an energy beam of the plurality of energy beams to at least one test vector based on at least one property of the test vector with respect to a predefined borderline in the working area. The test vector comprises at least one irradiation vector of the plurality of irradiation vectors. The method further includes obtaining an irradiation plan.

12 Claims, 4 Drawing Sheets

(56) References Cited

U.S. PATENT DOCUMENTS

| | | | |
|---|---|---|---|
| 10,589,382 B2 | 3/2020 | Roerig et al. | |
| 10,596,662 B2 | 3/2020 | Haro Gonzalez et al. | |
| 10,611,091 B2 | 4/2020 | Sterenthal et al. | |
| 10,668,534 B2 | 6/2020 | Mamrak et al. | |
| 10,688,593 B2 | 6/2020 | Roerig et al. | |
| 10,695,867 B2 | 6/2020 | Etter et al. | |
| 10,821,510 B2 | 11/2020 | Jakimov et al. | |
| 10,828,700 B2 | 11/2020 | Mamrak et al. | |
| 10,919,218 B2 | 2/2021 | Mamrak et al. | |
| 10,974,457 B2 | 4/2021 | Roesgen et al. | |
| 11,065,820 B2 | 7/2021 | Umang et al. | |
| 11,072,025 B2 | 7/2021 | Martin et al. | |
| 2013/0112672 A1 | 5/2013 | Keremes et al. | |
| 2015/0174827 A1* | 6/2015 | Schwarze | B29C 64/393 700/120 |
| 2016/0082668 A1 | 3/2016 | Perret et al. | |
| 2016/0282848 A1 | 9/2016 | Hellestam | |
| 2017/0113410 A1 | 4/2017 | Fruth | |
| 2017/0173736 A1 | 6/2017 | Gray | |
| 2017/0173737 A1 | 6/2017 | Gray | |
| 2017/0173883 A1 | 6/2017 | Gray et al. | |
| 2017/0320264 A1 | 11/2017 | Herzog et al. | |
| 2017/0341175 A1 | 11/2017 | Ladewig et al. | |
| 2018/0093416 A1 | 4/2018 | Prexler et al. | |
| 2018/0147669 A1 | 5/2018 | Narayanan et al. | |
| 2018/0272611 A1 | 9/2018 | Cantzler et al. | |
| 2018/0281112 A1* | 10/2018 | Roerig | B29C 64/153 |
| 2018/0345409 A1 | 12/2018 | Pavlov et al. | |
| 2018/0370146 A1 | 12/2018 | Domröse et al. | |
| 2019/0054566 A1* | 2/2019 | Crear | G06F 3/1204 |
| 2019/0126413 A1 | 5/2019 | Bogdan, Jr. et al. | |
| 2019/0263065 A1 | 8/2019 | Huber et al. | |
| 2019/0315051 A1 | 10/2019 | Stadlmann | |
| 2019/0375012 A1 | 12/2019 | Wiesner et al. | |
| 2020/0156313 A1 | 5/2020 | Lehmann | |
| 2020/0164580 A1 | 5/2020 | Werner | |
| 2020/0206817 A1 | 7/2020 | Ray et al. | |
| 2020/0238623 A1 | 7/2020 | Umang et al. | |
| 2020/0261977 A1 | 8/2020 | Mamrak et al. | |
| 2020/0316717 A1 | 10/2020 | Plas et al. | |
| 2021/0053119 A1 | 2/2021 | Geisen | |
| 2021/0114111 A1 | 4/2021 | Schade et al. | |
| 2021/0129226 A1 | 5/2021 | Ploshikhin | |
| 2021/0170484 A1 | 6/2021 | Buhr | |
| 2021/0178480 A1 | 6/2021 | Mamrak et al. | |
| 2021/0178665 A1 | 6/2021 | Mamrak et al. | |
| 2021/0187830 A1 | 6/2021 | McCarthy et al. | |
| 2022/0001614 A1 | 1/2022 | Fey | |
| 2022/0024122 A1 | 1/2022 | Hagedorn et al. | |
| 2022/0152934 A1* | 5/2022 | Ortner | B22F 12/45 |
| 2022/0193769 A1 | 6/2022 | Hoppe et al. | |

FOREIGN PATENT DOCUMENTS

| | | |
|---|---|---|
| CN | 107498052 A | 12/2017 |
| CN | 107866567 A | 4/2018 |
| CN | 108016034 B | 5/2018 |
| CN | 108437455 A | 8/2018 |
| CN | 109532003 A | 3/2019 |
| CN | 109877319 A | 6/2019 |
| CN | 110524883 A | 12/2019 |
| CN | 108817386 A | 2/2020 |
| CN | 210099217 U | 2/2020 |
| CN | 110893685 A | 3/2020 |
| CN | 111070685 A | 4/2020 |
| CN | 109434107 B | 5/2020 |
| CN | 108790180 A | 9/2020 |
| CN | 111842889 A | 10/2020 |
| CN | 112417646 A | 2/2021 |
| CN | 112743834 A | 5/2021 |
| CN | 110090956 A | 6/2021 |
| DE | 19953000 C2 | 4/2003 |
| DE | 102005014483 A1 | 10/2006 |
| DE | 102016222261 A1 | 5/2018 |
| DE | 102016222559 A1 | 5/2018 |
| DE | 102017202843 B3 | 7/2018 |
| DE | 102017205051 A1 | 9/2018 |
| DE | 102017205053 A1 | 9/2018 |
| DE | 102017107364 A1 | 10/2018 |
| DE | 102017212565 A1 | 1/2019 |
| DE | 102017127148 A1 | 5/2019 |
| DE | 102017220153 A1 | 6/2019 |
| DE | 102018203233 A1 | 9/2019 |
| DE | 102018128279 A1 | 5/2020 |
| DE | 102018129028 A1 | 5/2020 |
| DE | 102019116214 A1 | 12/2020 |
| DE | 102019211846 A1 | 2/2021 |
| EP | 2875897 B1 | 1/2016 |
| EP | 3120967 A1 | 1/2017 |
| EP | 2999561 B1 | 2/2017 |
| EP | 2983898 B1 | 3/2017 |
| EP | 3077872 B1 | 2/2018 |
| EP | 3218168 A1 | 6/2018 |
| EP | 2991818 B1 | 7/2018 |
| EP | 3233336 B1 | 9/2018 |
| EP | 3083203 B1 | 10/2018 |
| EP | 2926979 B1 | 5/2019 |
| EP | 3248719 B1 | 5/2019 |
| EP | 3165349 B1 | 7/2019 |
| EP | 3542927 A1 | 9/2019 |
| EP | 3572166 A1 | 11/2019 |
| EP | 3610970 A1 | 2/2020 |
| EP | 3414044 B1 | 4/2020 |
| EP | 3202524 B1 | 5/2020 |
| EP | 3650206 A1 | 5/2020 |
| EP | 3174692 B1 | 6/2020 |
| EP | 3527352 B1 | 6/2020 |
| EP | 3666523 A1 | 6/2020 |
| EP | 3300885 B1 | 7/2020 |
| EP | 3113933 B1 | 10/2020 |
| EP | 3722079 A1 | 10/2020 |
| EP | 3730234 A1 | 10/2020 |
| EP | 3383624 B1 | 11/2020 |
| EP | 3269473 B1 | 1/2021 |
| EP | 3643480 B1 | 6/2021 |
| EP | 3630390 B1 | 7/2021 |
| EP | 3626433 B1 | 8/2021 |
| JP | 6872922 B2 | 5/2021 |
| JP | 6892957 B1 | 6/2021 |
| KR | 101819105 B1 | 1/2018 |
| KR | 102012236 B1 | 8/2019 |
| WO | WO 2016110440 A1 | 7/2016 |
| WO | WO 2017100811 A1 | 6/2017 |
| WO | WO 2017187147 A1 | 11/2017 |
| WO | WO 2019002232 A1 | 1/2019 |
| WO | WO 2019113949 A1 | 6/2019 |
| WO | WO 2019161886 A1 | 8/2019 |
| WO | WO 2019226463 A1 | 11/2019 |
| WO | WO 2020178216 A1 | 9/2020 |
| WO | WO 2020249619 A1 | 12/2020 |
| WO | WO 2021037954 A1 | 3/2021 |
| WO | WO 2021057725 A1 | 4/2021 |
| WO | WO 2021058216 A1 | 4/2021 |
| WO | WO 2021069124 A1 | 4/2021 |
| WO | WO 2021069647 A1 | 4/2021 |
| WO | WO 2021114600 A1 | 6/2021 |

* cited by examiner

METHOD AND PLANNING DEVICE FOR PLANNING A LOCALLY SELECTIVE IRRADIATION OF A WORKING AREA, COMPUTER PROGRAM, METHOD AND MANUFACTURING DEVICE FOR ADDITIVELY MANUFACTURING AN OBJECT FROM A POWDER MATERIAL

CROSS REFERENCE TO RELATED APPLICATIONS

This application claims benefit to European Patent Application No. EP 22160041.4, filed on Mar. 3, 2022, which is hereby incorporated by reference herein.

FIELD

Embodiments of the present invention relate to a method for planning a locally selective irradiation of a working area, a planning device for planning a locally selective irradiation of a working area, a computer program for carrying out such method, a method for additively manufacturing an object from a powder material, and a manufacturing device for carrying out such method.

BACKGROUND

In order to accelerate the process time for manufacturing an object or workpiece, in methods and apparatuses which use multiple energy beams for selectively irradiating a working area to solidify or consolidate powder material arranged in form of a powder material layer in the working area, the different energy beams are displaced simultaneously along different irradiation vectors over the powder material layer. The decision which energy beam will irradiate a particular region is typically taken ad hoc or at least separately for each workpiece. It is therefore not reproducible or even foreseeable which laser will irradiate which region. This approach meets its limits where workpieces or objects are subject to certification, in particular when they must fulfil certain quality requirements with respect to security or safety, in particular in the fields of aerospace engineering. In this case, it should be possible to know beforehand for each individual to-be-manufactured object, which energy beam is assigned to which region. It is further advantageous to avoid any hard borderline between regions assigned to different energy beams since this could otherwise lead to the formation of imperfections or pores. However, algorithms which aim to overcome the aforementioned problems tend to be complicated and come with high demands with respect to processing power.

SUMMARY

Embodiments of the present invention provide a method for planning a locally selective irradiation of a working area with a plurality of energy beams by displacing the plurality of energy beams along a plurality of irradiation vectors over a powder material layer of a powder material arranged in the working area. The method includes assigning an energy beam of the plurality of energy beams to at least one test vector based on at least one property of the test vector with respect to a predefined borderline in the working area. The test vector comprises at least one irradiation vector of the plurality of irradiation vectors. The method further includes obtaining an irradiation plan.

BRIEF DESCRIPTION OF THE DRAWINGS

Subject matter of the present disclosure will be described in even greater detail below based on the exemplary figures. All features described and/or illustrated herein can be used alone or combined in different combinations. The features and advantages of various embodiments will become apparent by reading the following detailed description with reference to the attached drawings, which illustrate the following.

DETAILED DESCRIPTION

Embodiments of the present invention provide a method for planning a locally selective irradiation of a working area, a planning device for planning a locally selective irradiation of a working area, a computer program for carrying out such method, a method for additively manufacturing an object from a powder material, and a manufacturing device for carrying out such method.

According to a first aspect, embodiments of the present invention provide a—in particular computer-implemented—method for planning a locally selective irradiation of a working area—herein further referred to as "planning method"—with a plurality of energy beams by displacing the plurality of energy beams along a plurality of irradiation vectors over a powder material layer of a powder material arranged in the working area, comprising: i) assigning an energy beam of the plurality of energy beams to at least one test vector, the test vector comprising at least one irradiation vector of the plurality of irradiation vectors, on the basis of at least one property of the test vector with respect to a predefined borderline in the working area, and ii) obtaining an irradiation plan. By providing the predefined borderline and assigning the energy beam to the test vector depending on the at least one property of the test vector, the method according to embodiments of the invention implements a predictable and reproducible approach to decide which laser beam will be assigned to which region of the working area. Thus, the method is in particular applicable to the manufacturing of objects subject to certification, in particular in the field of aerospace engineering. Furthermore, because the method relies only on the property of the test vector itself, no particular complicated algorithm is necessary, and the method is easy to implement and does not demand high processing power.

The test vector may be an irradiation vector of the plurality of irradiation vectors. Alternatively, the test vector may comprise at least two, in particular adjacent or concatenated, irradiation vectors. In particular, the test vector may be a coherent vector, the coherent vector consisting of at least two adjacent or concatenated irradiation vectors.

In the context of the present technical teaching, an irradiation vector is understood to mean in particular a continuous, preferably linear, displacement of the energy beam in the working area over a certain distance with a certain direction of displacement. The irradiation vector includes in particular the direction or orientation of the displacement, i.e. the vector orientation. The irradiation vector, in particular if it is a contour vector, does not have to be formed as a straight line section at all, rather an irradiation vector, formed in particular as a contour vector, can also follow a line or curve that is curved at least in some areas.

In the context of the present technical teaching, a contour vector is understood to mean, in particular, a special irradiation vector extending along a contour line. A contour line is understood to mean, in particular, an imaginary boundary line of the object to be manufactured in a respective powder material layer, that is, in particular, an imaginary boundary line or border of a cross-sectional area of the object to be manufactured, the cross-sectional area lying in the powder material layer. In particular, the contour vector preferably locally follows the shape of the contour line in the section of the contour line assigned to the contour vector.

In the context of the present technical teaching, a coherent vector is understood to mean a path defined by at least two adjacent or concatenated irradiation vectors.

In particular, the borderline is a virtual borderline. In particular, the borderline is only virtually defined in the working area. In particular, the borderline is not associated with any physical demarcation in the working area.

Additive or generative manufacturing or production of an object or workpiece is understood to mean in particular a manufacturing process selected from a group, consisting of selective laser sintering, laser metal fusion (LMF), direct metal laser melting (DMLM), laser net shaping manufacturing (LNSM), selective electron beam melting ((S)EBM), and laser engineered net shaping (LENS). Accordingly, the manufacturing device disclosed below is particularly adapted to perform at least one of the aforementioned additive or generative manufacturing processes.

In particular, the energy beams each are selected from a group, consisting of an electromagnetic beam, in particular an optical working beam, in particular a laser beam, and a particle beam, in particular an electron beam. The optical working beam may be continuous or pulsed, in particular a continuous laser beam or a pulsed laser beam.

In an embodiment, the predefined borderline separates a first irradiation area of a plurality of irradiation areas from a second irradiation area of the plurality of irradiation areas, the irradiation areas being defined in the working area. The first irradiation area is assigned to a first energy beam of the plurality of energy beams, and the second irradiation area is assigned to a second energy beam of the plurality of energy beams. Step i) comprises: a1) determining whether the test vector crosses the predefined borderline, b) if the test vector crosses the predefined borderline, determining whether a greater portion of the test vector is located in the first irradiation area or in the second irradiation area, c) if the greater portion of the test vector is located in the first irradiation area, assigning the first energy beam to the test vector, and d) if the greater portion of the test vector is located in the second irradiation area, assigning the second energy beam to the test vector. This decision rule is referred to as the "greater-portion rule", wherein the decision rules described herein are generally referred to as "assignment rules". It allows for a particular simple and reproducible assignment of an energy beam to the respective test vector. Further, this rule advantageously helps to avoid a hard boundary between regions of the to-be-manufactured object, but rather generates a teethlike interconnection between a region irradiated by the first energy beam and a region irradiated by the second energy beam.

In particular, if the predefined borderline splits the test vector exactly into equal portions or halves, a first half being located in the first irradiation area and a second half being located in the second irradiation area, one of the following rules is applied: the test vector is split into a first sub-vector and a second sub-vector, and the first energy beam is assigned to the first sub-vector and the second energy beam is assigned to the second sub-vector; or, the test vector as a whole is assigned to one predetermined or ad hoc, in particular randomly, chosen energy beam, selected from the first energy beam and the second energy beam.

In an embodiment, the planning method comprises further: a2) determining whether the test vector crosses a predefined overlap area, the overlap area extending in a direction perpendicular to the predefined borderline, wherein the predefined borderline is arranged in the overlap area, and wherein the first and the second energy beams are both assigned to the overlap area, and, if the test vector crosses the overlap area, instead of steps b) to d), splitting the test vector in a first sub-vector and a second sub-vector according to a splitting rule in a step e), and f) assigning the first energy beam to the first sub-vector and assigning the second energy beam to the second sub-vector. This decision rule is referred to as the "transcending rule".

In particular, the overlap area extends symmetrically in both directions perpendicular to the predefined borderline.

In the context of the present technical teaching, that the test vector crosses the predefined overlap area is understood to mean that the test vector transcends the overlap area in both directions.

In particular, the splitting rule is predetermined, or ad hoc selected, in particular in accordance with a predetermined selection rule, or randomly. In particular, the splitting may be selected automatically, or manually by a human operator.

If otherwise the test vector does not cross the overlap region but is only partially located in the overlap region, it is further determined whether the test vector crosses the predefined borderline. If this is the case, the "greater-portion rule" is applied. If instead the test vector does not cross the predefined borderline, the "one-area rule" as defined below is applied.

In an embodiment, the splitting rule of step e) is selected from a group, consisting of: the test vector is split at the predefined borderline; the test vector is split at a splitting locus—or point—within the overlap area, wherein the splitting locus is chosen in order to minimize a length difference between the first sub-vector and the second sub-vector; and the test vector is split at a boundary line delimiting the overlap area towards the irradiation area, in which a centre point—or centre of gravity—of the test vector is located, in particular if the centre point of the test vector is located outside the overlap area.

In particular, that the splitting locus is chosen in order to minimize the length difference between the first sub-vector and the second sub-vector is understood to mean that that the splitting locus is chosen such that the length difference between the first sub-vector and the second sub-vector is minimized. In a particular embodiment, the test vector is bisected or divided in half.

In an embodiment, coherent vectors, in particular, contour vectors, of the plurality of irradiation vectors, at least where the coherent vectors belong to a same line, in particular contour line, of an object to be produced, are assigned to a same energy beam of the plurality of energy beams. However, this may not in all situations for all devices be feasible, e. g. where an energy beam may not reach, or not reach completely, inside an irradiation area assigned to another energy beam but rather only up to a demarcation line. In this case, and in particular only in this case, the coherent vector or contour line is divided at such a predefined—hard—demarcation line, and irradiation vectors of the coherent vector or contour line which are located on one side of the demarcation line are assigned to one energy beam, wherein such irradiation vectors located on the other side of the demarcation line are assigned to another energy beam. If in particular an irradiation vector crosses the demarcation line, the irradiation vector is either split at the demarcation line, or the "greater-portion rule" is analogously applied with respect to the demarcation line. The demarcation line is defined in addition to the predefined borderline and/or the overlap area. In particular, for the coherent vectors, the predefined borderline and/or the overlap area is ignored, and the assignment of the laser beam is made only with respect to the demarcation line. This subset of rules is also referred to as the "coherence rule".

In the alternative, coherent vectors may be treated like other test vectors, i. e. according to any other rule, or, coherent vectors which are contour vectors are treated according to the "coherence rule", whereas other coherent vectors, which are not contour vectors, are treated like other test vectors.

In an embodiment, the planning method comprises further: a3) determining whether the test vector is completely arranged in one of the irradiation areas as a determined area, and, if the test vector is completely arranged in one of the irradiation areas as a determined area, instead of any of steps b) to f), assigning the energy beam assigned to the determined area to the test vector in a step g). This decision rule is also referred to as the "one-area rule".

In particular, that the test vector is completely arranged in one of the irradiation areas is understood to mean that the test vector does not cross any predefined borderline.

In particular, the steps a1), a2), a3) need not necessarily be carried out in this order. Rather, the steps are on the same hierarchy level and may be carried out in any order.

In an embodiment, the method steps, in particular steps a1) to g), are carried out for the test vector with respect to at least one further predefined—virtual— borderline as the predefined borderline, the at least one further predefined borderline separating a specific irradiation area of the plurality of irradiation areas assigned to a specific energy beam of the plurality of energy beams from another specific irradiation area of the plurality of irradiation areas assigned to another specific energy beam of the plurality of energy beams. In particular, there may be more than two energy beams, and, respectively, more than two irradiation areas, making it desirable to have more than one predefined borderline between the different irradiation areas. In particular, at least one of the specific irradiation area and the other specific irradiation area is different from the first or the second irradiation area. In particular, at least one of the specific irradiation area and the other specific irradiation area is a third irradiation area. In particular, at least one of the specific energy beam and the other specific energy beam is different from the first or the second energy beam. In particular, at least one of the specific energy beam and the other specific energy beam is a third energy beam. Specifically: a second predefined borderline may separate the second irradiation area assigned to a second energy beam from a third irradiation area assigned to a third energy beam, and so forth. In particular, if there are n energy beams and n irradiation areas, there are (n-1) predefined borderlines, or n predefined borderlines, depending on the concrete arrangement of the irradiation areas in a row or in a loop or circle.

In an embodiment, the method steps, in particular steps a1) to g), are carried out for each irradiation vector of the plurality of irradiation vectors, including or excluding coherent vectors, as the test vector. If the method steps are carried out for each irradiation vector excluding coherent vectors, the excluded coherent vectors are treated according to the "coherence rule". In particular, the method is carried out as an iterative process, in particular successively iterating steps a1) to g) for one irradiation vector after the other as the test vector.

In the alternative, the method steps, in particular steps a1) to g), are carried out for a selection of irradiation vectors of the plurality of irradiation vectors—preferably successively, in an iterative process—as the test vector. In particular, the selection may include or exclude coherent vectors, where excluded coherent vectors are treated according to the "coherence rule".

In particular, steps a1) to g) are carried out for a plurality of powder material layers arranged in a temporal layer sequence—one after the other, in temporal succession—in the working area. In this way, a three-dimensional object, in particular a three-dimensional workpiece or component, is produced layer-by-layer. In particular, steps a1) to g) are carried out in or for each powder material layer.

In particular, at least one borderline is defined prior to step i) and used as the predefined borderline or as the at least one further predefined borderline.

In addition or in the alternative, at least one overlap area is defined prior to step i) and used as the predefined overlap area.

In an embodiment, the predefined borderline is constant relative to the working area in at least a plurality of the powder material layers, preferably in each powder material layer. In particular, each predefined borderline is constant within this meaning.

In an embodiment, an operator of a planning device or manufacturing device implementing the method may configure the location of at least one of the predefined borderline and the boundary lines which to delimit the overlap area. Preferably, the planning device or manufacturing device has a display unit which is configured to display the working area and the at least one of the predefined borderline and the boundary lines. Further, preferably the operator may configure the location of at least one of these lines by manipulating the respective representation on the display units, most preferably on a touchscreen of the display unit, in a visual and intuitive manner.

Additionally, or in the alternative, the operator may select at least one assignment rule, or a set of assignment rules, in particular a splitting rule to be applied with the "transcending rule".

In a second aspect, the object is in particular achieved by providing a method for additively manufacturing an object from a powder material—hereinafter referred to as "manufacturing method"—, comprising the following steps: providing an irradiation plan obtained by means of a planning method according to the invention or according to at least one of the embodiments as disclosed above, for the locally selective irradiation of a working area with a plurality of energy beams, and manufacturing the object according to the irradiation plan. With respect to the manufacturing method, in particular the same advantages are achieved as explained above in relation to the planning method.

In an embodiment, the irradiation plan is obtained by carrying out the planning method according to the invention or according to at least one of the embodiments as disclosed above.

In particular, for manufacturing of the object, each irradiation vector is processed with the respective energy beam assigned to the irradiation vector in accordance with the irradiation plan.

In a third aspect, the object is in particular achieved by providing a computer program comprising instructions which, when the computer program is executed on a computing device, cause the computing device to carry out a planning method according to the invention or according to at least one of the embodiments as disclosed above.

In addition, or in the alternative, the computer program comprises instructions which, when the computer program is executed on a computing device, cause the computing device to carry out a manufacturing method according to the invention or according to at least one of the embodiments as disclosed above. With respect to the computer program, in particular the same advantages are achieved as explained above in relation to the planning method and to the manufacturing method.

In a fourth aspect, the object is in particular achieved by providing a planning device for planning a locally selective irradiation of a working area with a plurality of energy beams in order to manufacture an object from a powder material arranged in the working area, wherein the planning device is adapted to carry out a planning method according to the invention or according to at least one of the embodiments as disclosed above. With respect to the planning device, in particular the same advantages are achieved as explained above in relation to the planning method, to the manufacturing method, and to the computer program.

In particular, the planning device comprises means for carrying out a planning method according to the invention or according to at least one of the embodiments as disclosed above.

In an embodiment, the planning device is designed as a device selected from a group consisting of a computer, in particular a personal computer (PC), a plug-in card or driver card, and an FPGA board. In one embodiment, the planning device is an RTC5 or RTC6 control card of SCANLAB GmbH, in particular in the embodiment currently available on the date determining the priority of the present teaching.

In particular, the planning device may be provided externally or separately to a manufacturing device, wherein a data set is preferably created by the planning device, which is then transmitted in a suitable manner, for example by means of a data carrier or via a network, in particular via the Internet, or via another suitable wireless or wired form of transmission, to the manufacturing device, in particular a control device of the manufacturing device. However, the planning device can also be integrated into a manufacturing device. In particular, the planning device can be integrated into the control device of the manufacturing device, or the control device of the manufacturing device can be designed as a planning device, in particular by providing a suitable hardware component and/or by implementing a suitable computer program, in particular software. However, it is also possible for the planning device to comprise a plurality of computing devices, in which case, in particular, it is designed to be physically distributed. Preferably, the planning device then comprises a plurality of interconnected computing devices. In particular, the planning device can be designed as a data cloud, or the planning device is part of a data cloud. In another embodiment, it is also possible for the planning device to comprise, on the one hand, at least one computing device external to the manufacturing device and, on the other hand, the manufacturing device, in particular the control device of the manufacturing device, in which case steps performed by the planning device are performed partly on the external computing device and partly on the manufacturing device, in particular on the control device. In particular, it is also possible that the planning device does not take over the complete planning of the locally selective irradiation of the working area, but only parts thereof; in particular, it is possible that the planning device takes over only that part of the planning of the locally selective irradiation of the working area which relates to the steps and/or determinations described above. Other parts of the planning of the locally selective irradiation, on the other hand, can be carried out in other computing devices, in particular in computing devices external to the manufacturing device, or also in the manufacturing device itself, in particular its control device, or in a data cloud.

In a fifth aspect, the object is in particular achieved by providing a manufacturing device for additively manufacturing objects from a powder material, having at least one beam generating device adapted to generate a plurality of energy beams, at least one scanning device adapted to locally selectively irradiate a working area with the plurality of energy beams to produce an object from the powder material disposed in the working area by displacing the plurality of energy beams along a plurality of irradiation vectors over the working area, and a control device operatively connected to the scanning device and adapted to control the scanning device, wherein the control device is adapted to carry out a manufacturing method according to the invention or according to at least one of the embodiments as disclosed above. With respect to the manufacturing device, in particular the same advantages are achieved as explained above in relation to the planning method, to the manufacturing method, the computer program and the planning device.

The scanning device preferably comprises at least one scanner, in particular a galvanometer scanner, piezo scanner, polygon scanner, MEMS scanner, and/or a working head or processing head displaceable relative to the working area. The scanning devices proposed herein are particularly suitable for displacing the energy beams within the working area along a plurality of irradiation vectors.

A working head or processing head displaceable relative to the working area is in particular understood to mean an integrated component of the manufacturing device, which has at least one radiation outlet for at least one energy beam, the integrated component, that is the working head, being displaceable as a whole relative to the working area along at least one displacement direction, preferably along two displacement directions perpendicular to each other. Such a working head can in particular be of portal design, or be guided by a robot. In particular, the working head can be designed as a robot hand of a robot.

In particular, the beam generating device is a laser, or comprises a plurality of lasers. The energy beams then are advantageously generated as intense beams of coherent electromagnetic radiation, in particular coherent light. In this respect, "irradiation" preferably means "exposure to light".

In particular, at least two energy beams of the plurality of energy beams are adapted to be displaced over the complete working area. In a particular embodiment, all energy beams are adapted to be displaced over the complete working area. In the alternative, not all the energy beams, but only a certain number of energy beams out of the plurality of energy beams are adapted to be displaced over the complete working area. In another embodiment, none of the energy beams is adapted to be displaced over the complete working area, but the energy beams, or at least a subset of energy beams, share a common irradiation area, delimited by the demarcation lines. If this common irradiation area is relatively small, the demarcation lines may correspond to the boundary lines delimiting the overlap area, and thus the common irradiation area may correspond to the overlap area. If the common irradiation area is relatively large, the demarcation lines may be defined in a distance to the boundary lines, and the common irradiation area may in particular be larger than the overlap area. Specifically, the common irradiation area may completely include the overlap area as an enclave.

In an embodiment, he manufacturing device is adapted for selective laser sintering. Alternatively, or additionally, the manufacturing device is adapted for selective laser melting.

In an embodiment, the control device is selected from a group consisting of a computer, in particular a personal computer (PC), a plug-in card or driver card, and an FPGA board. In a preferred embodiment, the control device is an RTC5 or RTC6 control card from SCANLAB GmbH, in particular in the embodiment currently available on the date determining the priority of the present teaching.

Figure 1:
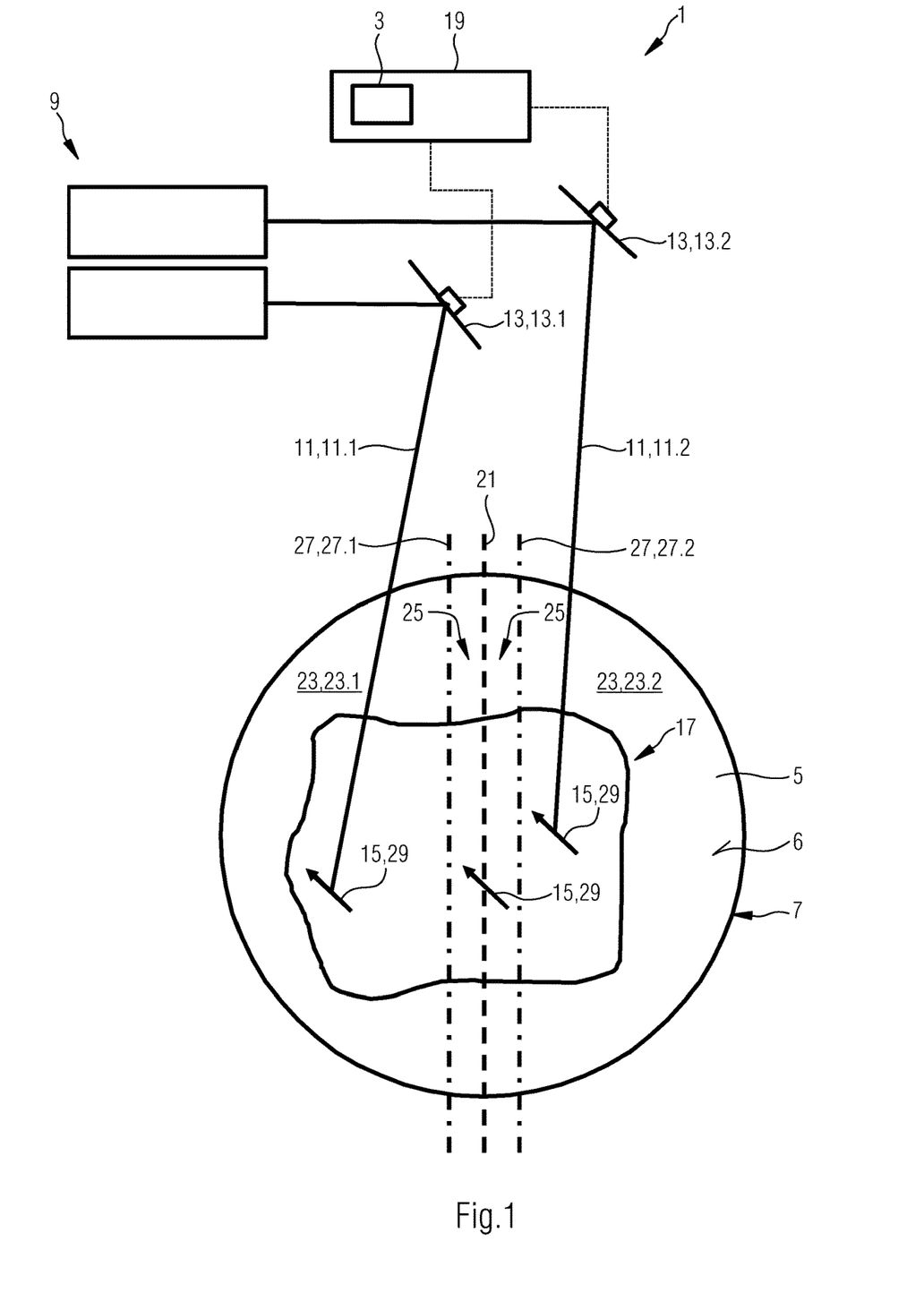
FIG. 1 shows a manufacturing device comprising a planning device according to some embodiments.

FIG. 1 shows an embodiment of a manufacturing device 1 comprising an embodiment of a planning device 3.

The manufacturing device 1 is adapted to additively manufacture an object 17 from a powder material 5, arranged in form of powder material layers 6—layer-by-layer—in a working area 7. The manufacturing device 1 has a beam generating device 9 adapted to generate a plurality of energy beams 11, in particular laser beams, wherein FIG. 1 shows a first energy beam 11.1 and a second energy beam 11.2. The manufacturing device 1 further has a scanning device 13 comprising a first scanner 13.1 and a second scanner 13.2, for displacing the energy beams 11 along a plurality of irradiation vectors 15 over the working area 7, such that the working area 7 is locally selectively irradiated with the energy beams 11 to produce the object 17 from the powder material 5 disposed in the working area 7. Still further, the manufacturing device 1 has a control device 19 operatively connected to the scanning device 13 and adapted to control the scanning device 13.

In the embodiment of FIG. 1, the control device 19 comprises the planning device 3. The planning device 3 is adapted to carry out a planning method according to an embodiment as explained below with respect to FIGS. 2 to 6.

The manufacturing device 1 is adapted to carry out a manufacturing method comprising the steps of providing an irradiation plan obtained by means of the planning method, and manufacturing the object 17 according to the irradiation plan.

FIG. 1 further shows a virtual predefined borderline 21 separating a first irradiation area 23.1 of two irradiation areas 23 defined in the working area 7 from a second irradiation area 23.2. The first irradiation area 23.1 is assigned to the first energy beam 11.1 and the second irradiation area 23.2 is assigned to the second energy beam 11.2. Further, an overlap area 25, in which the predefined borderline 21 is located, is assigned to both energy beams 11. Two virtual boundary lines 27 delimit the overlap area 25, the boundary lines 27 being symmetrically arranged at both sides of and parallel to the predefined borderline 21, a first boundary line 27.1 delimiting the overlap area 25 towards the first irradiation area 23.1, and a second boundary line 27.2 delimiting the overlap area 25 towards the second irradiation area 23.2.

The planning method comprises i) assigning an energy beam 11 of the energy beams 11 to at least one test vector 29, the test vector 29 comprising at least one irradiation vector 15 of the plurality of irradiation vectors 15, on the basis of at least one property of the test vector 29 with respect to the predefined borderline 21 in the working area 7, and ii) obtaining the irradiation plan.

Figure 2:
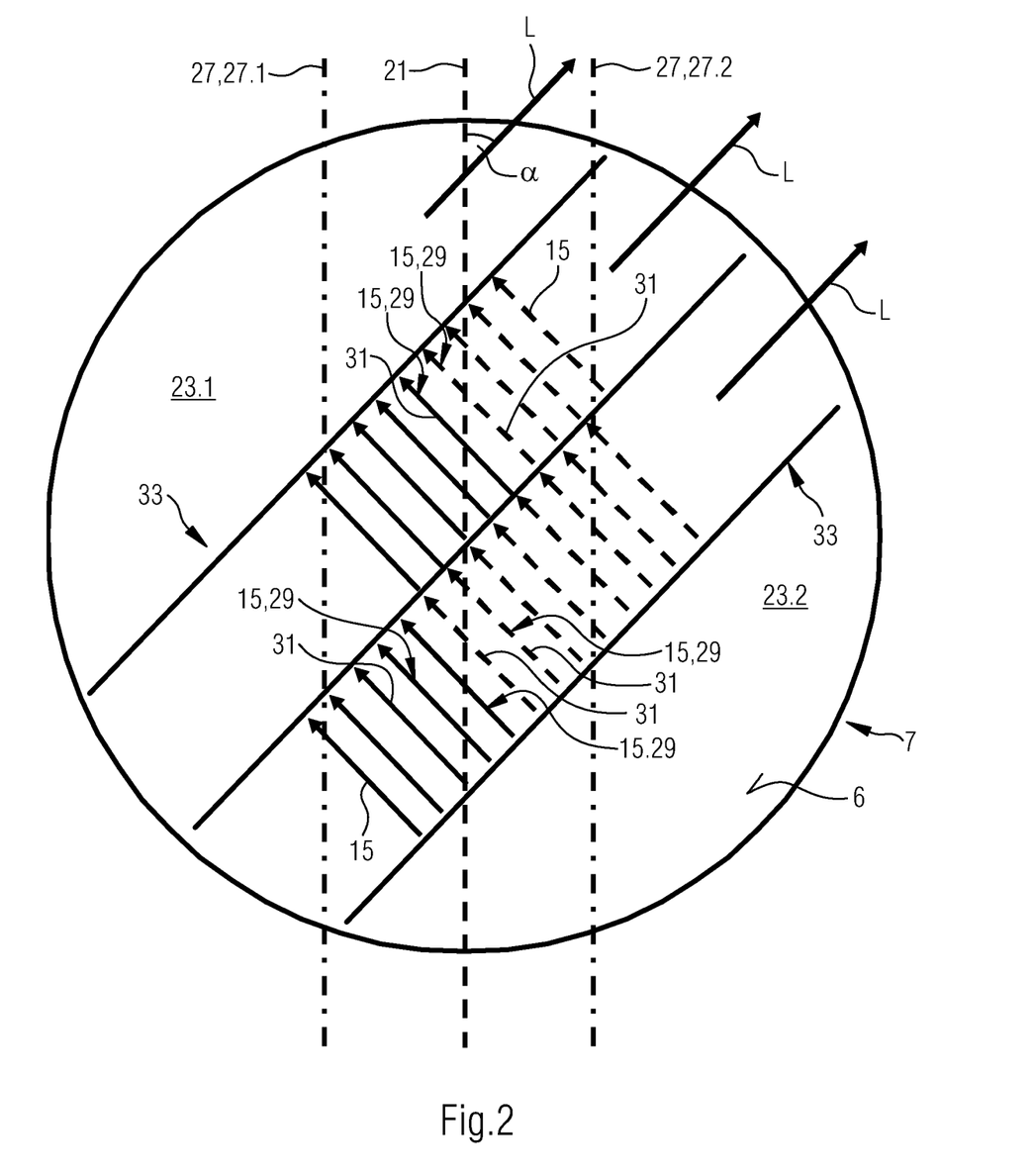
FIG. 2 shows a first embodiment of a planning method for planning a locally selective irradiation of a working area with a plurality of energy beams to be carried out by the planning device according to FIG. 1.

FIG. 2 shows a first embodiment of a planning method for planning a locally selective irradiation of the working area 7 with a plurality of energy beams 11 to be carried out by the planning device 3 according to FIG. 1.

The same or functionally equivalent elements are assigned the same reference numerals in all figures, such that reference is made in each case to the preceding explanations.

In this first embodiment, step i) comprises: a1) determining whether the test vector 29 crosses the predefined borderline 21. If b) the test vector 29 crosses the predefined borderline 21, determining whether a greater portion 31 of the test vector 29 is located in the first irradiation area 23.1 or in the second irradiation area 23.2. If c) the greater portion 31 of the test vector 29 is located in the first irradiation area 23.1, the first energy beam 11.1 is assigned to the complete test vector 29. If otherwise d) the greater portion 31 of the test vector 29 is located in the second irradiation area 23.2, the second energy beam 11.2 is assigned to the test vector 29 ("greater-portion rule"). This is schematically shown for a small number of irradiation vectors 15 as test vectors 29 in FIG. 2, and the laser beam 11 assigned to each of these test vectors 29 is indicated: Insofar, irradiation vectors 15 assigned to the first energy beam 11.1 are drawn as solid lines, and irradiation vectors 15 assigned to the second energy beam 11.2 are drawn as dashed lines. This indication scheme applies to all the FIGS. 2 to 5.

If the predefined borderline 21 splits the test vector 29 exactly into equal portions or halves, a first half being located in the first irradiation area 23.1 and a second half being located in the second irradiation area 23.2, one of the following rules is applied: the test vector is split into a first sub-vector and a second sub-vector, and the first energy beam is assigned to the first sub-vector and the second energy beam is assigned to the second sub-vector; or the test vector as a whole is assigned to one predetermined or ad hoc, in particular randomly, chosen energy beam 11, selected from the first energy beam 11.1 and the second energy beam 11.2.

In particular, in FIG. 2, the working area 7 is irradiated in form of parallel stripes 33, each stripe 33 comprising a length direction L, and consisting of a plurality of irradiation vectors 15 oriented perpendicular to the length direction L of the respective stripe 33 and extending over the whole width of the stripe 33. The length directions L of the stripes 33 form an angle α to the predefined borderline 21. As a person skilled in the art may readily acknowledge, for each stripe 33 exists a certain point on the predefined borderline, where the assignment of the laser beams 11 to the irradiation vectors 15 of the stripe 33 switches from the first laser beam 11.1 to the second laser beam 11.2. Thus, a teethlike irradiation pattern results with respect to the different laser beams 11, and a hard linear boundary is avoided. Preferably, the angle α is varied, in particular rotating the stripes 33, from powder material layer 6 to powder material layer 6 making the object 17 extremely stable, in particular by avoiding misalignments, defects or pores.

Figure 3:
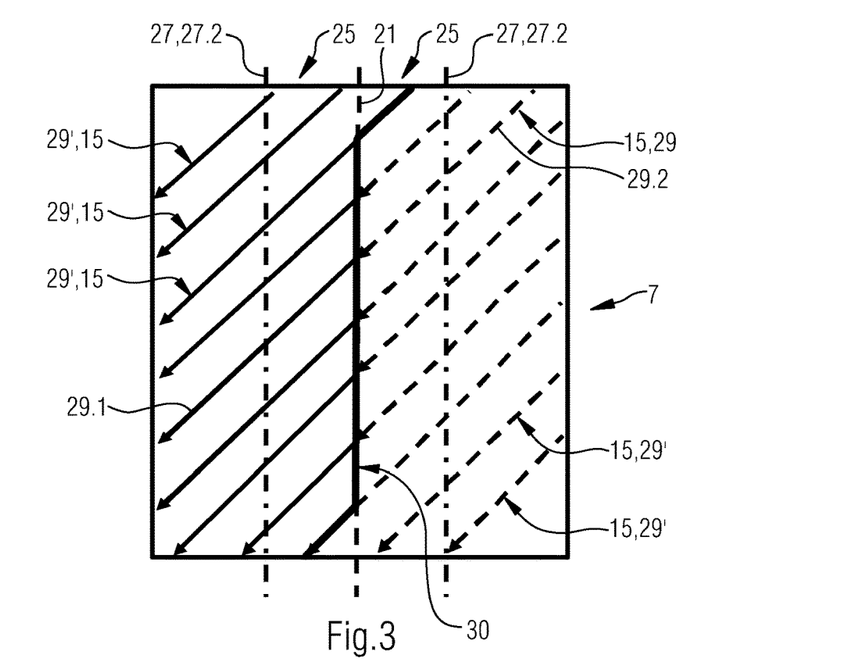
FIG. 3 shows a second embodiment of the planning method.

FIG. 3 shows a second embodiment of the planning method. In this second embodiment, the planning method comprises further: a2) determining whether the test vector 29 crosses the predefined overlap area 25; if the test vector 29 crosses the overlap area 25, instead of steps b) to d), e) splitting the test vector 29 in a first sub-vector 29.1 and a second sub-vector 29.2 according to a splitting rule; and f) assigning the first energy beam 11.1 to the first sub-vector 29.1 and assigning the second energy beam 11.2 to the second sub-vector 29.2 ("transcending rule").

In the embodiment of FIG. 3, splitting the test vectors 29 at the predefined borderline 21 is applied as the splitting rule.

FIG. 3 also shows other test vectors 29' which do not completely cross the overlap region 25 but are only partially located in the overlap region 25. In this case, it is further determined whether the other test vectors 29' cross the predefined borderline 21. If this is the case, the "greater-portion rule" is applied. If instead one of the other test vectors 29' does not cross the predefined borderline 21, the "one-area rule" applied, determining a3) whether the other test vector 29' is completely arranged in one of the irradiation areas 25 as a determined area, and, if the other test vector 29' is completely arranged in one of the irradiation areas 25 as a determined area, instead of any of steps b) to f), assigning g) the energy beam 11 assigned to the determined area to the other test vector 29'.

FIG. 3 further shows a limit line 30 between the regions irradiated by the first energy beam 11.1 on the one hand and by the second energy beam 11.2 on the other hand, the limit line 30 resulting from applying the respective assignment rules as explained with relation to FIG. 3.

Figure 4:
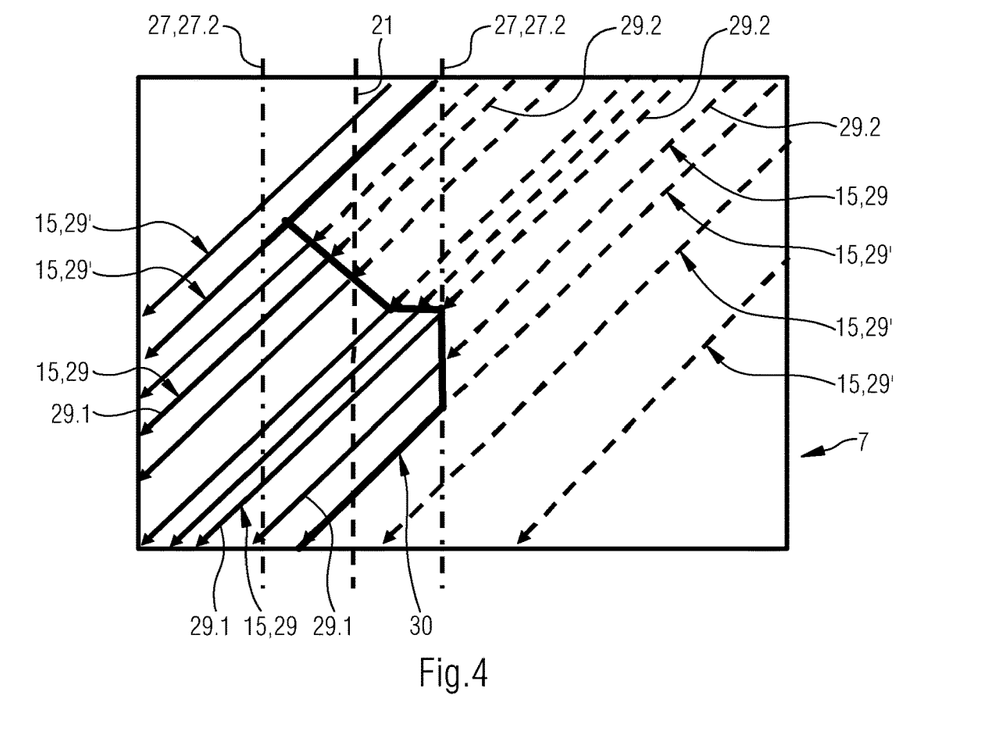
FIG. 4 shows a third embodiment of the planning method.

FIG. 4 shows a third embodiment of the planning method. In this third embodiment, splitting the test vectors 29 at a splitting locus within the overlap area 25 is applied as the splitting rule, wherein the splitting locus is chosen in order to minimize a length difference between the first sub-vector 29.1 and the second sub-vector 29.2. In particular, the test vectors 29 are split in half, and the locus is a centre point of the respective test vector 29. However, if the centre point of a test vector 29 is located outside the overlap area 25, the respective test vector 29 instead is split at the boundary line 27 delimiting the overlap area 25 towards the irradiation area 23, in which the centre point of the test vector 29 is located.

FIG. 4 also shows other test vectors 29' which do not completely cross the overlap region 25 but are only partially located in the overlap region 25. In this case, it is further determined whether the other test vector 29' crosses the predefined borderline 21. If this is the case, the "greater-portion rule" is applied. If instead the other test vector 29' does not cross the predefined borderline 21, the "one-area rule" is applied.

Again, irradiation vectors 15 assigned to the first energy beam 11.1 are drawn as solid lines, and irradiation vectors 15 assigned to the second energy beam 11.2 are drawn as dashed lines. The set of rules according to the third embodiment helps to avoid splitting the irradiation vectors 15 at a hard boundary to a greater extent than the set of rules according to the second embodiment shown in FIG. 3, as is immediately clear from the respective limit lines 30.

Figure 5:
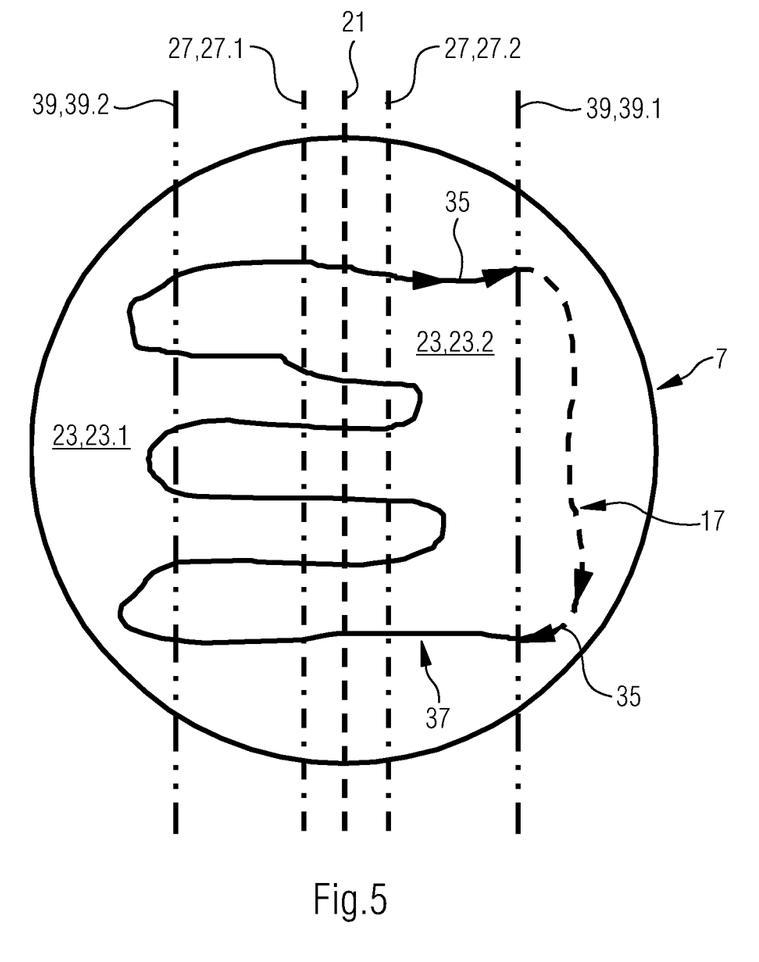
FIG. 5 shows a fourth embodiment of the planning method.

FIG. 5 shows a fourth embodiment of the planning method, in particular as a further development of the aforementioned embodiments. In this fourth embodiment, contour vectors 35 as an example of coherent vectors, which belong to a same contour line 37, of the object 17 to be produced, are assigned to a same energy beam 11.

However, this may not in all situations for all devices be feasible, e. g. where an energy beam 11 may not reach, or not reach completely, inside an irradiation area 23 assigned to another energy beam 11. In this case, and in particular only in this case, the contour line 37 is divided at predefined— hard— demarcation line 39, and contour vectors 35 which are located on one side of the respective demarcation line 39 are assigned to one energy beam 11, wherein such contour vectors 35 located on the other side of the demarcation line 39 are assigned to the other energy beam 11 ("coherence rule"). In the embodiment shown here, the first energy beam 11.1 only reaches up to a first demarcation line 39.1, and the second energy beam 11.2 only reaches up to a second demarcation line 39.2. The contour line 37 is divided at the first demarcation line 39.1, and all contour vectors 35 on the left side of the first demarcation line 39.1 are assigned to the first energy beam 11.1—as indicated by a solid part of the contour line 37—, and all contour vectors 35 on the right side of the first demarcation line 39.1 are assigned to the second energy beam 11.2—as indicated by a dashed part of the contour line 37 —. The demarcation lines 39 are defined in addition to the predefined borderline 21 and the overlap area 25.

While subject matter of the present disclosure has been illustrated and described in detail in the drawings and foregoing description, such illustration and description are to be considered illustrative or exemplary and not restrictive. Any statement made herein characterizing the invention is also to be considered illustrative or exemplary and not restrictive as the invention is defined by the claims. It will be understood that changes and modifications may be made, by those of ordinary skill in the art, within the scope of the following claims, which may include any combination of features from different embodiments described above.

The terms used in the claims should be construed to have the broadest reasonable interpretation consistent with the foregoing description. For example, the use of the article "a" or "the" in introducing an element should not be interpreted as being exclusive of a plurality of elements. Likewise, the recitation of "or" should be interpreted as being inclusive, such that the recitation of "A or B" is not exclusive of "A and B," unless it is clear from the context or the foregoing description that only one of A and B is intended. Further, the recitation of "at least one of A, B and C" should be interpreted as one or more of a group of elements consisting of A, B and C, and should not be interpreted as requiring at least one of each of the listed elements A, B and C, regardless of whether A, B and C are related as categories or otherwise. Moreover, the recitation of "A, B and/or C" or "at least one of A, B or C" should be interpreted as including any singular entity from the listed elements, e.g., A, any subset from the listed elements, e.g., A and B, or the entire list of elements A, B and C.

The invention claimed is:

1. A method for planning a locally selective irradiation of a working area with a plurality of energy beams by displacing the plurality of energy beams along a plurality of irradiation vectors over a powder material layer of a powder material arranged in the working area, the method comprising:

assigning an energy beam of the plurality of energy beams to at least one test vector, the test vector comprising at least one irradiation vector of the plurality of irradiation vectors and representing a linear displacement of the energy beam over a distance in a displacement direction, wherein the assigning the energy beam to the at least one test vector is based on whether the test vector crosses a predefined borderline or a predefined overlap area in the working area, wherein the predefined borderline separates a first irradiation area from a second irradiation area of a plurality of irradiation areas, the predefined borderline being arranged in the predefined overlap area, and obtaining an irradiation plan based on the assigning the energy beam of the plurality of energy beams.

2. The method according to claim 1, wherein the assigning the energy beam to the at least one test vector comprises:
   determining whether the test vector crosses the predefined borderline,
   upon determining that the test vector crosses the predefined borderline, determining whether a greater portion of the test vector is located in the first irradiation area or in the second irradiation area,
   upon determining that the greater portion of the test vector is located in the first irradiation area, assigning a first energy beam to the test vector, and
   upon determining that the greater portion of the test vector is located in the second irradiation area, assigning a second energy beam to the test vector.

3. The method according to claim 1, wherein the assigning the energy beam to the at least one test vector comprises:
   determining whether the test vector crosses the predefined overlap area, and
   upon determining that the test vector crosses the overlap area:
      splitting the test vector into a first sub-vector and a second sub-vector according to a splitting rule, and
      assigning a first energy beam to the first sub-vector and assigning a second energy beam to the second sub-vector.

4. The method according to claim 3, wherein the splitting rule is selected from a group consisting of:
   the test vector is split at the predefined borderline,
   the test vector is split at a splitting locus within the overlap area, wherein the splitting locus is chosen in order to minimize a length difference between the first sub-vector and the second sub-vector, and
   the test vector is split at a boundary line delimiting the overlap area towards one of the first irradiation area and the second irradiation area, in which a centre point of the test vector is located.

5. The method according to claim 1, further comprising:
   assigning another energy beam to another test vector with respect to at least one further predefined borderline, the at least one further predefined borderline separating a specific irradiation area of the plurality of irradiation areas assigned to a specific energy beam of the plurality of energy beams from another specific irradiation area of the plurality of irradiation areas assigned to another specific energy beam of the plurality of energy beams.

6. The method according to claim 1, wherein the step of assigning the energy beam to at least one test vector comprises:
   determining whether the test vector is completely arranged in one of a plurality of irradiation areas, and
   upon determining that the test vector is completely arranged in a specific irradiation area of the plurality of irradiation areas,
   assigning the energy beam assigned to the specific irradiation area to the test vector.

7. The method according to claim 1, wherein the step of assigning an energy beam of the plurality of energy beams is carried out for:
   each irradiation vector of the plurality of irradiation vectors as the test vector, or
   a selection of irradiation vectors of the plurality of irradiation vectors as the test vector.

8. The method according to claim 1, wherein the predefined borderline is constant relative to the working area in at least a plurality of powder material layers.

9. A method for additively manufacturing an object from a powder material, the method comprising: providing an irradiation plan obtained by a method according to claim 1, and manufacturing the object according to the irradiation plan.

10. A manufacturing device for additively manufacturing objects from a powder material, the manufacturing device comprising:
   at least one beam generating device adapted to generate a plurality of energy beams,
   at least one scanning device adapted to locally selectively irradiate a working area with the plurality of energy beams to produce an object from the powder material disposed in the working area by displacing the plurality of energy beams along a plurality of irradiation vectors over the working area, and
   a control device operatively connected to the scanning device and adapted to control the scanning device, wherein
   the control device is adapted to carry out a method according to claim 9.

11. A non-transitory computer-readable medium having instructions stored thereon, the instructions, when executed on a computing device, causing the computing device to carry out a method according to claim 1.

12. A planning device for planning a locally selective irradiation of a working area with a plurality of energy beams in order to manufacture an object from a powder material arranged in a working area, wherein the planning device is adapted to carry out a method according to claim 1.

* * * * *